(12) United States Patent
Fantuzzi et al.

(10) Patent No.: US 11,197,690 B2
(45) Date of Patent: Dec. 14, 2021

(54) INTEGRATED EXPANDABLE ACCESS FOR MEDICAL DEVICE INTRODUCER

(71) Applicant: Abiomed, Inc., Danvers, MA (US)

(72) Inventors: Glen R. Fantuzzi, Arlington, MA (US); Thorsten Siess, Wuerselen (DE)

(73) Assignee: Abiomed, Inc., Danvers, MA (US)

( * ) Notice: Subject to any disclaimer, the term of this patent is extended or adjusted under 35 U.S.C. 154(b) by 176 days.

(21) Appl. No.: 16/130,475

(22) Filed: Sep. 13, 2018

(65) Prior Publication Data
US 2019/0076167 A1    Mar. 14, 2019

Related U.S. Application Data

(60) Provisional application No. 62/558,507, filed on Sep. 14, 2017.

(51) Int. Cl.
*A61B 17/34*    (2006.01)
*A61M 60/135*    (2021.01)
(Continued)

(52) U.S. Cl.
CPC ...... *A61B 17/3462* (2013.01); *A61B 17/3415* (2013.01); *A61B 17/3423* (2013.01);
(Continued)

(58) Field of Classification Search
CPC .............. A61M 1/125; A61M 25/0668; A61M 2025/0004; A61M 2025/0024;
(Continued)

(56) References Cited

U.S. PATENT DOCUMENTS

| | | | | |
|---|---|---|---|---|
| 5,190,528 A | * | 3/1993 | Fonger | A61M 25/01 477/63 |
| 5,503,631 A | * | 4/1996 | Onishi | A61M 25/1027 604/103.07 |
| 5,961,499 A | * | 10/1999 | Bonutti | A61B 17/0401 604/164.11 |
| 6,090,072 A | * | 7/2000 | Kratoska | A61B 17/3439 604/164.01 |

(Continued)

FOREIGN PATENT DOCUMENTS

| WO | 02/49537 A2 | 6/2002 | |
|---|---|---|---|
| WO | 2016/001439 A1 | 1/2016 | |
| WO | WO-2016001439 A1 * | 1/2016 | ............ A61M 39/02 |

OTHER PUBLICATIONS

International Search Report for International Patent Application No. PCT/US2018/050794, dated May 2, 2019.

*Primary Examiner* — Shefali D Patel
*Assistant Examiner* — Avery Smale
(74) *Attorney, Agent, or Firm* — Botos Churchill IP Law LLP

(57) ABSTRACT

An integrated sheath assembly for inserting a medical device such as a percutaneous pump into a vessel can include a first sheath having a first lumen defining a first opening between proximal and distal ends of the first sheath for passage of a portion of the pump and a second sheath having a second lumen defining a second opening between proximal and distal ends of the second sheath. The second lumen is expandable to allow passage of the first sheath containing the portion of the pump. The first sheath fills a space between the second sheath and the portion of the percutaneous pump when the first sheath containing the percutaneous pump is inserted into the second lumen. The first sheath has a first hub, and the second sheath has a second hub. In some embodiments, a single sheath and a movable connector can be integrated on the medical device.

25 Claims, 11 Drawing Sheets

(51) Int. Cl.
    *A61M 25/00*        (2006.01)
    *A61M 25/06*        (2006.01)
(52) U.S. Cl.
    CPC ..... *A61B 17/3439* (2013.01); *A61M 25/0668*
            (2013.01); *A61M 60/135* (2021.01); *A61B*
            *17/3431* (2013.01); *A61B 2017/348* (2013.01);
            *A61M 2025/0004* (2013.01); *A61M 2025/0024*
                                                (2013.01)
(58) Field of Classification Search
    CPC .............. A61M 60/135; A61M 60/857; A61M
                    25/0023; A61M 2025/0175; A61B
                    17/3462; A61B 17/3431; A61B 17/3439
    See application file for complete search history.

(56)            References Cited

U.S. PATENT DOCUMENTS

| | | | | |
|---|---|---|---|---|
| 6,231,498 | B1* | 5/2001 | Pfeiffer | A61B 5/028 600/18 |
| 7,022,100 | B1* | 4/2006 | Aboul-Hosn | A61M 1/125 604/6.11 |
| 2002/0095115 | A1* | 7/2002 | Schock | A61M 1/1072 604/96.01 |
| 2005/0015076 | A1* | 1/2005 | Giebmeyer | A61M 25/0111 604/544 |
| 2014/0276644 | A1* | 9/2014 | Nelson | A61M 25/005 604/527 |
| 2015/0343179 | A1* | 12/2015 | Schumacher | A61M 25/0111 604/171 |

\* cited by examiner

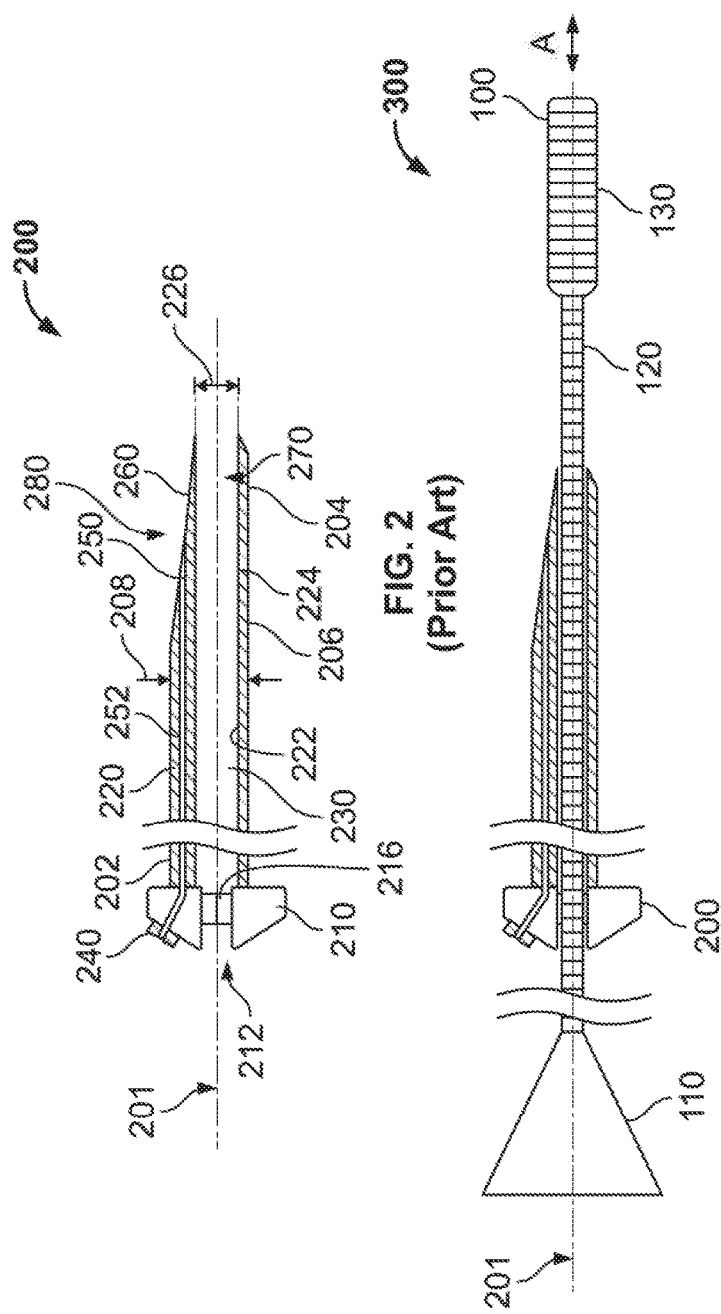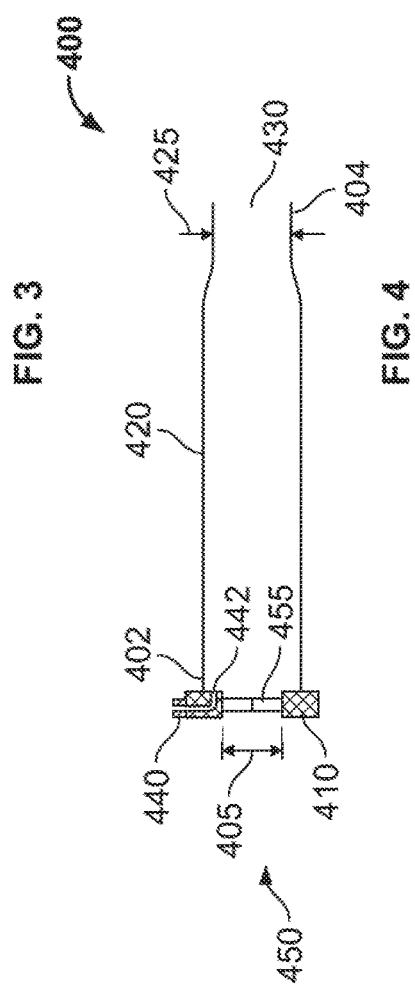

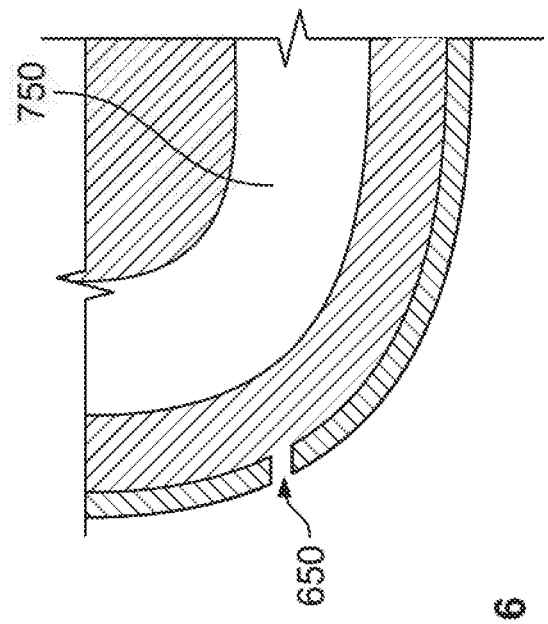
FIG. 6
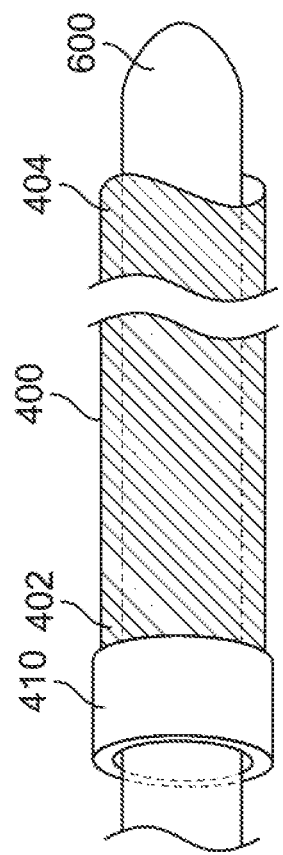

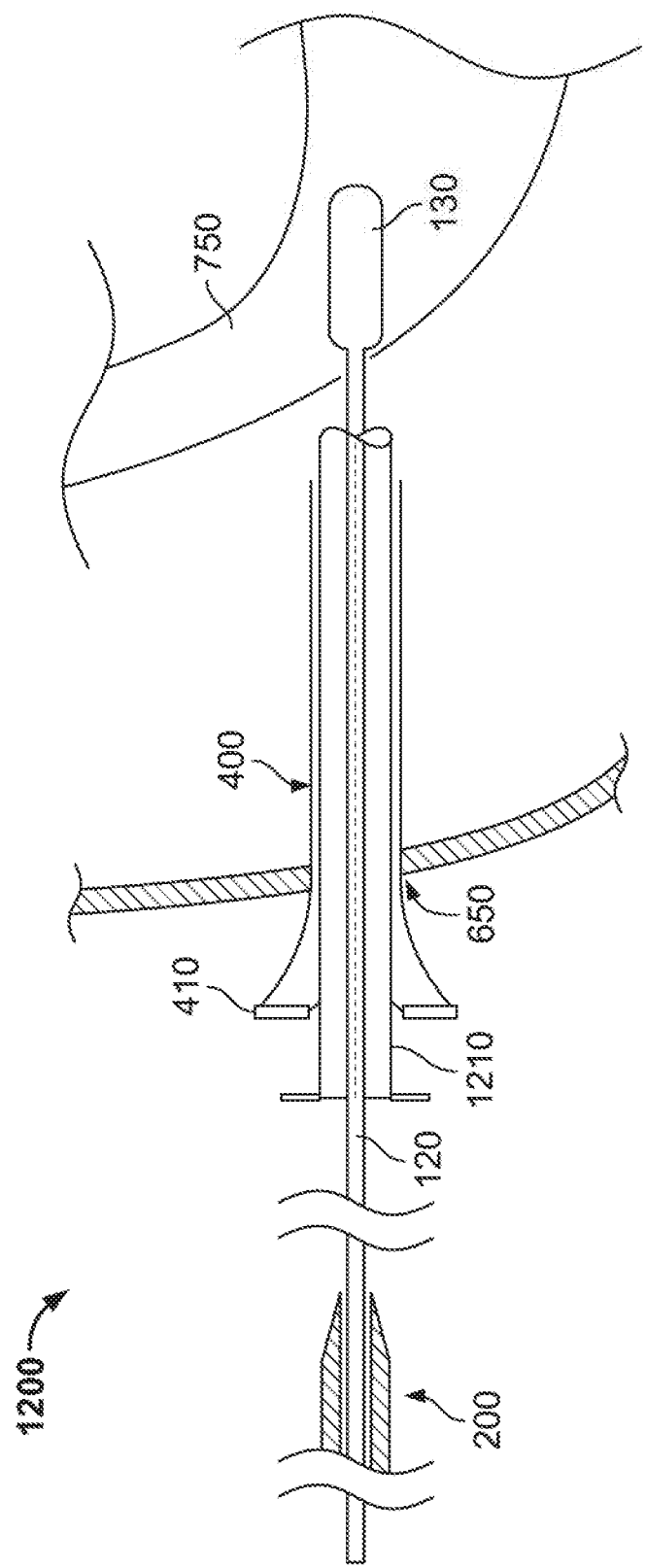

_US 11,197,690 B2_

INTEGRATED EXPANDABLE ACCESS FOR MEDICAL DEVICE INTRODUCER

CROSS-REFERENCE TO RELATED APPLICATIONS

This application claims priority to U.S. provisional application No. 62/558,507, filed on Sep. 14, 2017, the content of which is hereby incorporated herein by reference in its entirety.

BACKGROUND

A medical device, such as an intracardiac heart pump assembly, can be introduced into a patient in various ways. In general, a heart pump can be introduced in the heart to pump blood from the heart into a vessel to support the function of the heart. When deployed in the heart, a heart pump assembly pulls blood from the left ventricle of the heart and expels blood into the aorta, or pulls blood from the inferior vena cava (IVC) bypasses the right atrium and right ventricle and expels blood into the pulmonary artery. Heart pump assemblies are introduced surgically or percutaneously during a cardiac procedure through the vascular system. In one common approach, pump assemblies are inserted by a catheterization procedure through the femoral artery using a sheath, such as a peel-away introducer sheath. The sheath can alternatively be inserted in other locations such as in the femoral vein or any path for delivery of a pump for supporting either the left or right side of the heart.

The peel-away introducer sheath can be inserted into the femoral artery through an arteriotomy to create an insertion path for the pump assembly. A portion of the pump assembly is then advanced through an inner lumen of the introducer and into the artery. Once the pump assembly has been inserted, the peel-away introducer sheath is peeled away. A repositioning sheath can then be advanced over the pump assembly and into the arteriotomy. Replacing the introducer sheath with a sheath which does not need to be peeled away can prevent blood clot formation which would otherwise occur in the introducer sheath, and prevent or reduce bleeding at the insertion site in the skin and/or at the insertion site within the vessel because of better fixation of the sheath to the patient when used with a hemostatic valve.

Since peel-away introducer sheaths are not radially expandable, the inner diameter of the introducer sheath must always be large enough to accommodate the passage of the largest diameter of the heart pump inserted through the sheath, even if other parts of the pump assembly, such as the catheter, have a smaller diameter. This means that once the pump is inserted, the peel-away introducer creates an opening that has an outer diameter that is wider than necessary to allow passage of the pump catheter into the vessel. Accordingly, the peel-away introducer sheath is peeled away and replaced with a lower-profile repositioning sheath. But peeling away the introducer has several disadvantages. For example, peel-away introducers can peel too easily and risk being torn prematurely, leading to bleeding or vascular complications. On the other hand, peel-away introducers may require excessive force to peel away. If a physician applies too much force, when the introducer finally gives, the physician may inadvertently shift the position of the pump within the heart. Having to peel away the introducer also complicates the design of the hemostatic valve located in the hub of the introducer which also needs to separate. Additionally, the peel away action is an added step that the user must be aware and trained on, and which requires added time to perform.

Some medical introducers for applications other than inserting heart pumps have expandable sheath bodies which may expand radially to allow passage of percutaneous devices into the patient's vasculature. These introducers are inserted having inner diameters smaller than the outer diameter of the device being introduced. The introducers expand to allow passage of the device through the sheath and into the vasculature and then shrink again after the device has passed. In the current state, these expandable introducers are for relatively short term use and are stand-alone components. Since the current expandable sheaths are intended for short term use, they are not configured for preventing thrombosis between the sheath body and an indwelling catheter. Furthermore, the current expandable sheaths do not include means for sealing the arteriotomy for long durations or for preventing migration of the inserted device (in and out of the vessel).

SUMMARY OF INVENTION

Systems, devices and methods for insertion of a medical device (e.g., intravascular medical device) are presented. The devices are delivered through an expandable introducer sheath. Use of an introducer sheath capable of expansion allows a smaller puncture size to be used for insertion and can allow the vessel to more easily recoil to a smaller diameter after insertion of the pump. Additionally, because the medical device only momentarily passes through the vessel wall, the opening in the vessel is expected to be smaller than if a larger non-expandable sheath is used. Still further, since the medical device only momentarily passes through the vessel, if friction between the device, sheath, and vessel wall is minimized, there is a reduced axial load and reduced stress on the vessel. That is, the sheath is a smaller size and is not pushing or pulling the vessel along the axis of the insertion/removal path and instead, when the device passes through the vessel, the vessel is expanded outward radially. The expandable introducer sheath is configured to remain in an insertion path (e.g., an arteriotomy) for relatively long durations (e.g., >1 hr, >2 hr, >6 hr, or any suitable duration). To enable the introducer sheath to remain in the insertion path, the insertion sheath can be integrated with the percutaneous device being introduced or with a catheter associated with the percutaneous device. For example, the introducer sheath can connect to, or interlock with, a repositioning sheath of the mechanical assist device. In some implementations, the expandable introducer sheath is included in a repositioning sheath assembly.

By allowing the introducer sheath to connect to the repositioning sheath and remain in the insertion path, disadvantages associated with peel-away introducers can be avoided. For example, since the expandable introducer sheath need not be removed, the risk of premature peel-away is essentially eliminated and the risk of shifting the introduced device inadvertently (e.g., by overuse of force during peel-away) is reduced or eliminated. Furthermore, allowing the introducer sheath to remain in an insertion path simplifies the use of the introduced device by reducing the number of steps in the insertion procedure, namely by eliminating the peel-away process.

In a first aspect, a repositioning sheath assembly includes a first sheath having a first lumen defining a first opening between proximal and distal ends of the first sheath for the passage of a portion of the medical device, the first sheath having a first hub coupled to its proximal end. The assembly further includes a second sheath having a second lumen defining a second opening between proximal and distal ends of the second sheath, the second lumen being expandable to allow the passage of the first sheath containing the portion of the medical device, the second sheath having a second hub coupled to its proximal end. In this configuration, the first sheath fills a space between the second sheath and the portion of the medical device when the first sheath containing the portion of the medical device is inserted into the second lumen. As the space between the second sheath and the portion of the medical device is occupied by the first sheath, there is little to no additional space in which blood can accumulate. Accumulation of blood gives rise to thrombosis. Such an assembly can therefore reduce the risk of thrombus formation in the space between the first sheath and the second sheath, and in the space between the first sheath and the medical device. The assembly is advantageous over conventional peel-away introducer sheaths in that the expandable second sheath does not need to be separated or taken apart to make way for the first sheath.

In certain implementations, the sheath assembly includes a first port in fluid communication with a space between the first sheath and the portion of the medical device. In certain implementations, the first port is located on the first hub. In certain implementations, the sheath assembly includes a second port in fluid communication with a space between the second sheath and the first sheath when the first sheath is inserted into the second lumen. In certain implementations, the second port is located on the second hub. In certain implementations, the second hub comprises an opening that is in fluid communication with the first lumen of the first sheath. In certain implementations, the first sheath includes a further lumen parallel to the first lumen and extending from the proximal end to the distal end of the first sheath for the passage of a guidewire. In certain implementations, the first hub includes a third port in communication with the further lumen for passage of the guidewire.

In some implementations, the first sheath is geometrically tapered from its proximal to distal ends, an outer diameter of the first sheath at its proximal end being larger than the outer diameter of the first sheath at its distal end. In certain implementations, the first sheath comprises an expandable balloon for varying a diameter of the second lumen when the first sheath is inserted into the second lumen. In certain implementations, the first hub comprises a balloon port connected to the expandable balloon.

In some implementations, the first and second hubs are configured to couple to each other via at least one of: a threaded connection, a press fit connection and a clip-lock connection. In certain implementations, the first hub includes a feature configured for suturing to a patient. In certain implementations, the first hub includes a pair of suture wings, each wing having a plurality of ribs for securing sutures.

In certain implementations, the first sheath body is dimensioned to be introduced through a percutaneous access site of about 20 Fr (6.67 mm) or less. In certain implementations, the second sheath comprises either a porous material or a mesh material. In certain implementations, an external surface of the first sheath comprises one of: radiopaque markers, visible markers and markers for determining a depth of insertion. In certain implementations, an external surface of the first sheath is coated with one of: an antithrombogenic coating and a coating to reduce likelihood of blood clot formation between the first and second tubular sheaths. In certain implementations, an external surface of the first sheath is coated with one of: a hydrophilic coating, hydrophobic coating and a coating to reduce friction. In certain implementations, an external surface of the first sheath is coated with one of: an antimicrobial coating and a coating to reduce likelihood of infection occurring at the vessel aperture.

In some implementations, the first sheath and the second sheath are axially movable relative to one another a longitudinal axis. In certain implementations, the sheath assembly includes a catheter, and both of the first and second sheaths are slidably coupled to the catheter. In certain implementations, the medical device is percutaneous heart pump. In certain implementations, the second sheath is expandable by blood pressure within the blood vessel so as to seal a space between the first sheath and an arteriotomy in the blood vessel.

In further aspect, a repositioning sheath assembly includes a first rigid sheath having a first lumen defining a first opening between proximal and distal ends of the first sheath for the passage of a portion of the medical device. The assembly further includes a second sheath having a second lumen defining a second opening between proximal and distal ends of the second sheath, the second lumen being expandable to allow the passage of the first sheath containing the portion of the medical device, the second sheath having a second hub coupled to its proximal end, wherein the first sheath fills a space between the second sheath and the portion of the medical device when the first sheath containing the portion of the medical device is inserted into the second lumen. In this configuration, the sheath assembly facilitates delivery of the first and second sheaths and the portion of the medical device through the blood vessel, and wherein the first sheath is configured to be peeled away once the medical device is positioned in the blood vessel.

In certain implementations, the sheath assembly further includes a third sheath having a third lumen defining a third opening between proximal and distal ends of the third sheath for the passage of the portion of the medical device, the third sheath having a third hub coupled to its proximal end. In some implementations, the third hub is configured to be fluid communication with the second lumen when the third hub is coupled to the second hub.

In yet another aspect, a repositioning sheath assembly includes a first hub fixedly connected to the medical device, and a second sheath having a second lumen defining a second opening between proximal and distal ends of the second sheath. The second lumen is configured to be expandable to allow the passage of a portion of the medical device, the second sheath having a second hub coupled to its proximal end. Further, the first hub is configured to be in fluid communication with the second lumen when the first hub is coupled to the second hub. In certain implementations, the first hub comprises a first port in fluid communication with a space between the second sheath and the portion of the medical device when the first hub is coupled to the second hub.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 2 shows a cross section of an illustrative prior art repositioning sheath for providing to an opening formed in a vessel (e.g., an arteriotomy);

FIG. 3 shows a cross section of the illustrative repositioning sheath of FIG. 2 integrated with the medical device of FIG. 1;

FIG. 4 shows a cross section of an illustrative expandable sheath for arterial access for a medical device such as the device of FIG. 1;

FIG. 6 shows a perspective view of the illustrative expandable sheath of FIG. 4 being inserted into an insertion site using a vascular dilator;

FIG. 12 shows an implementation of an illustrative alternative configuration of an expandable sheath assembly inserted into a blood vessel through an arteriotomy wherein the expandable sheath of FIG. 4 is inserted with a rigid peel-away sheath.

DETAILED DESCRIPTION

To provide an overall understanding of the systems, method, and devices described herein, certain illustrative embodiments will be described. Although the embodiments and features described herein are specifically described for use in connection with a percutaneous heart pump system, it will be understood that all the components and other features outlined below may be combined with one another in any suitable manner and may be adapted and applied to other types of medical devices such as cardiac therapy and cardiac assist devices, including balloon pumps, cardiac assist devices implanted using a surgical incision, and the like.

The systems, methods and devices described herein provide a sheath assembly for the insertion of a medical device (e.g., a percutaneous heart pump) into a blood vessel through a vessel aperture. The sheath assembly comprises a first sheath having a first lumen defining a first open passage between proximal and distal ends of the first sheath. This allows a portion of a medical device to pass through the first sheath. The first sheath has a first hub coupled to its proximal end for attachment with other components of the integrated sheath assembly. The sheath assembly also comprises a second sheath having a second lumen defining a second open passage between proximal and distal ends of the second sheath. This allows the medical device and the first sheath to pass through the second lumen of the second sheath. The second sheath has a second hub coupled to its proximal end for mating with other components of the integrated sheath assembly, such as the first hub of the first sheath. Such a mating of hubs ensures that the first and second lumens are in fluid connection. The second lumen is constructed from an expandable material to allow the streamlined passage of the percutaneous pump and the first sheath. In this manner, the space between the first and second sheaths and the space between the body of the percutaneous medical device and the second sheath is minimized. This prevents or reduces accumulation of blood between (i) the first and second sheaths and (ii) the second sheath and the body of the percutaneous medical device, thereby preventing or reducing thrombosis in those spaces. The coupling between the expandable sheath and the repositioning sheath can be hemostatic and designed with a sealing feature such as an O-ring or interference fit to prevent blood leaking between the sheaths and the catheter.

Further, when the first sheath is inserted into the second lumen, the first sheath fills a space between the second sheath and the medical device such as a percutaneous pump. This prevents or reduces accumulation of blood between the second sheath and the percutaneous pump, further minimizing the risk of thrombosis. Once the hubs are coupled, fluid can be passed through the integrated expandable sheath assembly to continuously flush blood out of the space between the expandable sheath and the integrated sheath body.

Figure 1:
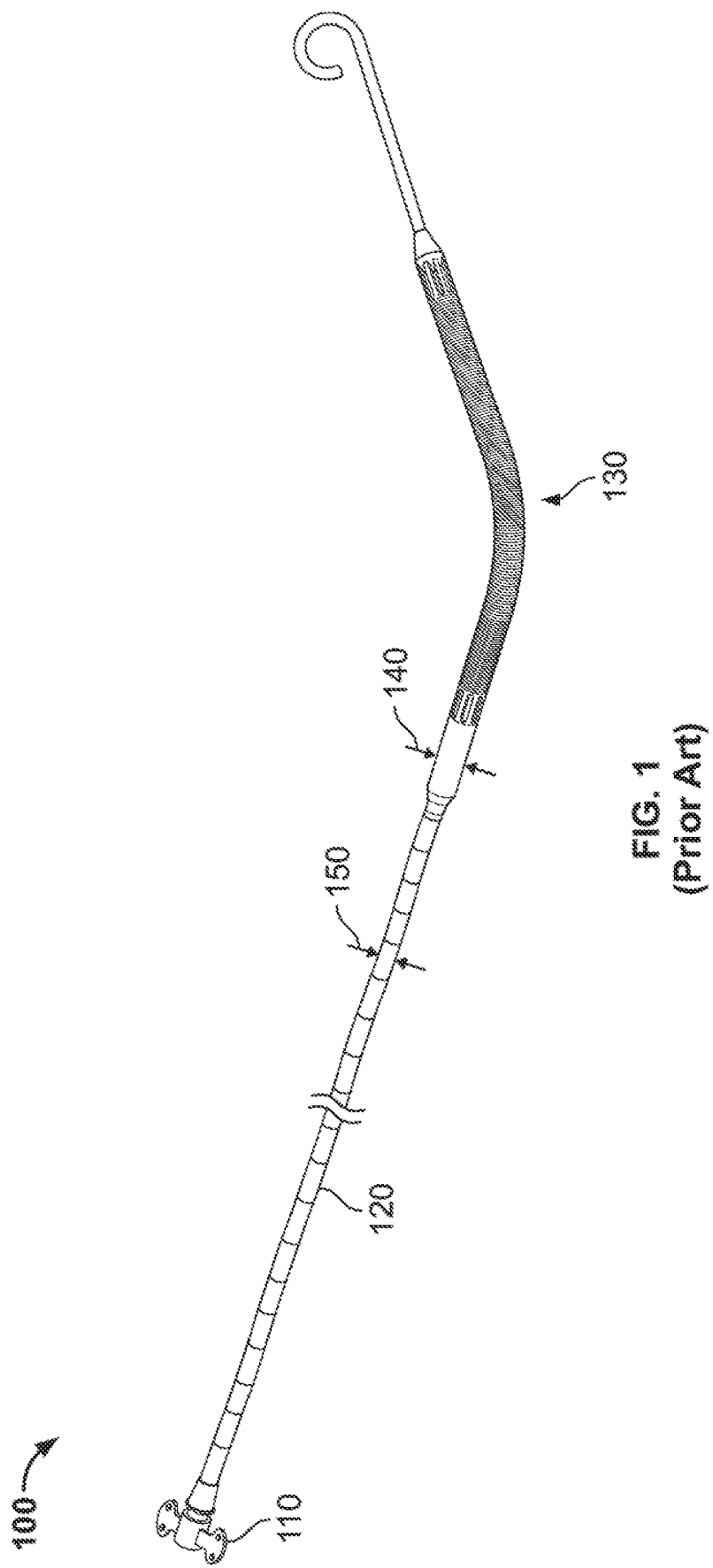
FIG. 1 shows a perspective view of an illustrative prior art medical device.

FIG. 1 shows an illustrative mechanical assist device (MAD) such as a percutaneous pump 100 according to certain implementations. The pump 100 comprises a pump handle 110, a pump head 130 and a pump body 120 connecting the pump handle 110 to the pump head 130. The pump body 120 is tubular and has a substantially uniform outer diameter. The pump body 120 enables the pump head 130 and the pump handle 110 to be in electro-mechanical communication. The pump handle 110 is in communication with control circuitry which allows the control of the pump head 130. The pump head 130 contains electro-mechanical components that enable the device to perform various tasks within the body of a patient, such as pump blood from a location within the body. The pump head 130 has a diameter 140 that is larger than the diameter 150 of the pump body 120. An example of such a percutaneous pump is the Impella 2.5™ system (Abiomed, Inc., Danvers, Mass.). It will be understood that while a percutaneous heart pump is described herein, any other percutaneous medical device can be used in conjunction with the present disclosure.

FIG. 2 shows an illustrative repositioning sheath 200 according to certain implementations. The repositioning sheath 200 comprises a sheath body 220 having a central longitudinal axis 201, a proximal end portion 202 and a distal end portion 204. The sheath body 220 has a substantially uniform cross-section, and is dimensioned for insertion into a blood vessel through a vessel aperture. In certain implementations, the sheath body 220 may be tubular with a circular or ellipsoidal cross-section and having a constant or a varying wall thickness. In some implementations, the sheath body 220 is dimensioned for insertion into a femoral artery through an arteriotomy. The majority of the sheath body 220 may have a substantially uniform outer diameter of about 10 Fr, 11 Fr, 12 Fr, 13, Fr, 14 Fr, 15 Fr, 16 Fr, 17 Fr, 20 Fr, or any other suitable diameter. The sheath body 220 may be dimensioned to be introduced through a percutaneous access site of about 20 Fr (6.67 mm) or smaller (e.g., 19 Fr, 18 Fr, 17 Fr, 16 Fr, 15 Fr, 14 Fr, 13 Fr, 12 Fr, 10 Fr, 9 Fr, 8 Fr, 6 Fr, or less). The sheath body 220 may have a length of about 80 mm, 100 mm, 120 mm, 140 mm, 160 mm, or any other suitable length. In some implementations, the sheath body 220 may be tapered.

The sheath body 220 has a first lumen 230 that extends along the length of the sheath body 220 from the proximal end portion 202 to the distal end portion 204 and is substantially parallel to the longitudinal axis 201. The first lumen 230 is defined by the inner surface 222 of the wall 224 of the sheath body 220. The sheath body 220 has a diameter 208 while the first lumen 230 has a diameter 226. The distal end portion 204 of the sheath body 220 includes a tapered surface 260 and a first opening 270 in fluid communication with the first lumen 230. The tapered surface 260 has an outer diameter graduated from 11 Fr to 15 Fr (3.667 mm to 5 mm). The graduation in outer diameter of the tapered surface 260 may permit the repositioning sheath 200 to be inserted to a variable insertion depth as necessary to adequately plug the gap between the percutaneous pump and the insertion site. The tapered surface 260 of the repositioning sheath 200 may allow the user to better seal off the arteriotomy at variety of diameters (controlled by the length of the tapered surface 260 that is advanced into the arteriotomy). The user could advance the tapered surface 260 of the repositioning sheath 200 until oozing/bleeding stops. Arteriotomy size varies from patient to patient depending on calcification, scar tissue, vessel size, and elasticity, for example. The tapered surface 260 of the repositioning sheath 200 would enable customization of the arteriotomy seal as required. The first lumen 230 is dimensioned to allow passage of a portion of the percutaneous pump 100 of FIG. 1 in which the diameter 226 of the first lumen 230 is larger than the diameter 150 of the pump body 120. Additionally, the diameter 226 of the first lumen 230 is smaller than the diameter 140 of the pump head 130. A hub 210 is located at the proximal end portion 202 of the repositioning sheath 200, and has a passageway 212 that is in fluid communication with the first lumen 230. The passageway 212 is configured with a valve 216, such as a hemostatic valve as described in U.S. patent application Ser. No. 15/245,982 entitled "Hemostatic Valve for Medical Device Introducer", the entire application which is hereby incorporated by reference its in entirety. The passageway 212 and valve 216 allows for the passage of at least a portion of a mechanical assist device, such as the percutaneous pump 100 of FIG. 1, within the repositioning sheath 200. The sheath body 220 may be made of a flexible material, such as polyether block amides or any other suitable polymer, to reduce the stress on the blood vessel aperture. The material may be selected to meet stiffness requirements for a specific medical procedure.

An outer surface 206 of the sheath body 220 may be coated with a hydrophilic coating or any other suitable coating to reduce frictional forces during insertion/removal of the repositioning sheath 200 into/from the vasculature. Just a distal portion of the sheath body 220 may be coated or the coating may completely cover the outer surface 206 of the sheath body 220. A hydrophilic coating can also prevent adhesions to the blood vessel wall. Such adhesions could damage the vessel if the sheath is removed after having been in the blood vessel for an extended period of time (e.g., many days). The risk of adhesion to the blood vessel wall can increase as the duration of a procedure increases. In some implementations, the outer surface 206 of the wall 224 of the repositioning sheath body 220 includes an antimicrobial coating or any other suitable coating to prevent or reduce infection risk. Additionally, in some implementations, the inner surface 222 of the first lumen 270 and the inner surface of the second lumen 280 include an antimicrobial coating or any other suitable coating to prevent or reduce infection risk. In further implementations, the outer surface 206 of the sheath body 220 includes depth markings. The depth markings may be pad-printed or laser-etched onto the outer surface 206. In certain implementations, the depth markings are radio-opaque. The depth markings may be in centimeters, inches, millimeters, or any other suitable unit of measurement or combination thereof.

In certain implementations, the sheath body 220 may have a second lumen 250, such as the second lumen in the dual lumen sheath described in U.S. patent application Ser. No. 14/827,741, entitled "Dual Lumen Sheath for Arterial Access," the entire application which is hereby incorporated by reference in its entirety. The second lumen 250 extends along the length of the sheath body 220 from the proximal end portion 202 to the distal end portion 204. The second lumen 250 is located within the wall 224 of the sheath body 220, and is offset from and substantially parallel to the longitudinal axis 201. The second lumen 250 has an opening 280 on the tapered surface 260 of the distal end portion 204 of the sheath body 220. Opening 280 is in fluid communication with the second lumen 250. In certain implementations, the hub 210 has a first port 240 in fluid communication with the second lumen 250. The first port 240 is affixed with a valve (not shown).

Further, in certain implementations, the repositioning sheath 200 may have an inflatable balloon attached to the outer surface 206 of the sheath body 220. The inflatable balloon may be in fluid communication with a second port located on the hub 210. During insertion of the repositioning sheath 200, the inflatable balloon may be in a collapsed state. In order to fix the position of the sheath at a particular depth of insertion in the arteriotomy, the balloon may be inflated with a fluid such as saline or air via the second port on the hub 210. The balloon can be formed from a flexible material, such as a polyurethane or Teflon material which can be inflated to a certain pressure that corresponds to a particular outer diameter. In certain aspects, the first port located on the hub is the balloon port.

As depicted in FIG. 3, the percutaneous pump 100 and the repositioning sheath 200 can be integrated to form a repositioning sheath assembly 300. The repositioning sheath 200 is fixed onto the body 120 of the percutaneous pump 100 such that the pump body 120 is positioned within the first lumen 230. As the diameter 226 of the first lumen 230 is smaller than the diameter 140 of the pump head 130, this enables integration of the percutaneous pump 100 and the repositioning sheath 200 during manufacturing where the pump head 130 is located exterior to the first opening 270 and prevents the percutaneous pump 100 from coming free from the repositioning sheath 200 prior to use. In this configuration, the pump 100 is able to move laterally (direction indicated by arrow A in FIG. 3) with respect to the repositioning sheath 200 thereby enabling the percutaneous pump 100 to be advanced into a blood vessel when the tapered surface 260 of the distal end 204 of the repositioning sheath 200 is plugged into the arteriotomy of the femoral artery of a patient.

FIG. 4 shows an expandable sheath 400 according to certain implementations. The expandable sheath 400 comprises an expandable body 420 having a proximal portion 402, a distal portion 404 and a lumen 430. The lumen 430 is open and connects the proximal portion 402 to the distal portion 404. A hub 410 is attached to the proximal portion 402 of the expandable body 420. The hub 410 has an opening 450 that is in fluid communication with the lumen 430. The opening 450 is configured with a valve 455, such as a hemostatic valve as described in U.S. patent application Ser. No. 15/245,982, the entire application which is hereby incorporated by reference in its entirety. The opening 450 has a diameter 405 which is designed to be larger than the diameter 208 of the sheath body 220 so as to allow the passage of the repositioning sheath assembly 300 within the lumen 430. In some implementations, the expandable body 420 may be tubular.

Figure 4A:
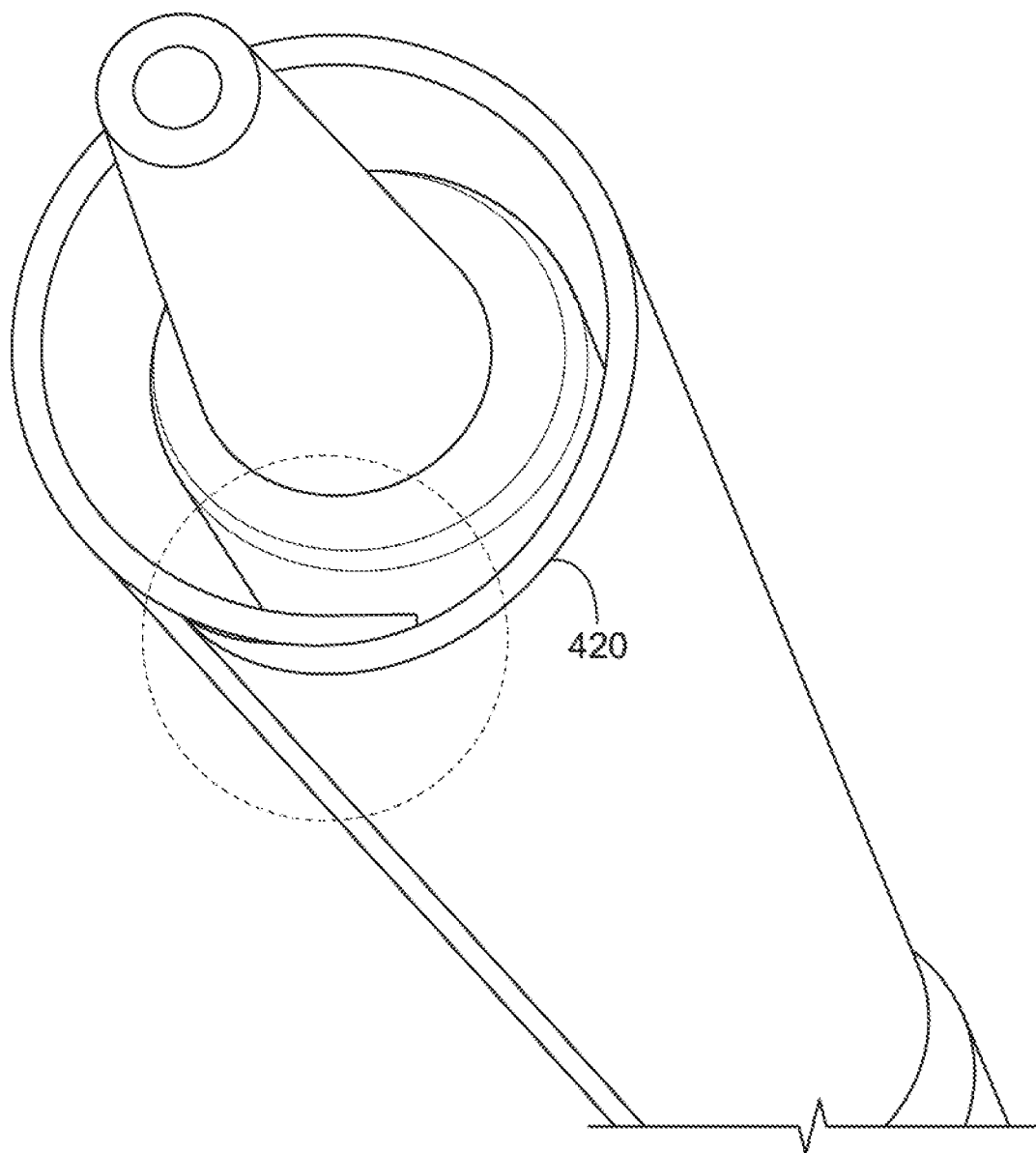
FIG. 4A shows a cross section of an illustrative expandable sheath comprising a sheet of compliant material rolled into a tubular configuration with ends that overlap.

The expandable body 420 has an unexpanded diameter 425. The expandable body 420 may be enlarged by an object inserted into the lumen 430. The expandable body 420 may be made from an expandable material that has a degree of compliance. Compliant materials such as polyester or polytetrafluoroethylene (PTFE) may be used, for example. In certain implementations, the expandable material may be a mesh made from a compliant material. In alternative implementations, the expandable sheath body 420 may comprise a porous material. In some implementations, the expandable sheath body 420 may comprise a sheet of compliant material rolled into a tubular configuration wherein the ends of the sheet overlap, as shown in FIG. 4A.

In some implementations, the unexpanded diameter 425 of the expandable body 420 may be larger than the diameter 150 of the pump body 120. The unexpanded diameter 425 of the expandable body 420 may be increased to accommodate the pump head 130 when the percutaneous pump 100 is inserted into the expandable sheath 400. The repositioning sheath 200 and the expandable sheath 400 form an expandable access assembly for advancement of a percutaneous device, such as the pump 100.

In some implementations, the expandable sheath 400 may have an inflatable balloon attached to the sheath body 420. The balloon may be inflated with a fluid such as saline or air via a balloon port on the hub 410 (not shown). The balloon can be formed from a flexible material, such as a polyurethane or Teflon material which can be inflated to a certain pressure that corresponds to a particular outer diameter. In certain aspects, the flushing port 440 located on the hub 410 is the balloon port.

In certain implementations, the hub 410 has a flushing port 440 connected to a passageway 442. The flushing port 440 is affixed with a valve (not shown). The passageway 442 is in fluid communication with the lumen 430. The flushing port 440 therefore enables a space between the expandable body 420 and the sheath body 220 to be flushed with fluid when the integrated repositioning sheath 300 is inserted into the expandable sheath 400. A pressure bag may be connected to the flushing port 440 using any kind of engaging mechanism (e.g. threads, clip lock, etc.). The pressure bag can be used to flush the space between the expandable body 420 and the sheath body 220 with a fluid to maintain the patency said space thereby preventing any blood clots from forming. Such flushing may be instantaneous or continuous. An infusion pump may be used in combination with the pressure bag to regulate the flow rate of liquid into the patient. For example, the flow rate may be limited to 1 mL/hr, 2 mL/hr, 5 mL/hr, 10 mL/hr, or any other suitable flow rate. The port can also be used to obtain measurement of blood pressure if necessary. Alternatively, any of the hubs herein may not include a flushing port.

Figure 5:
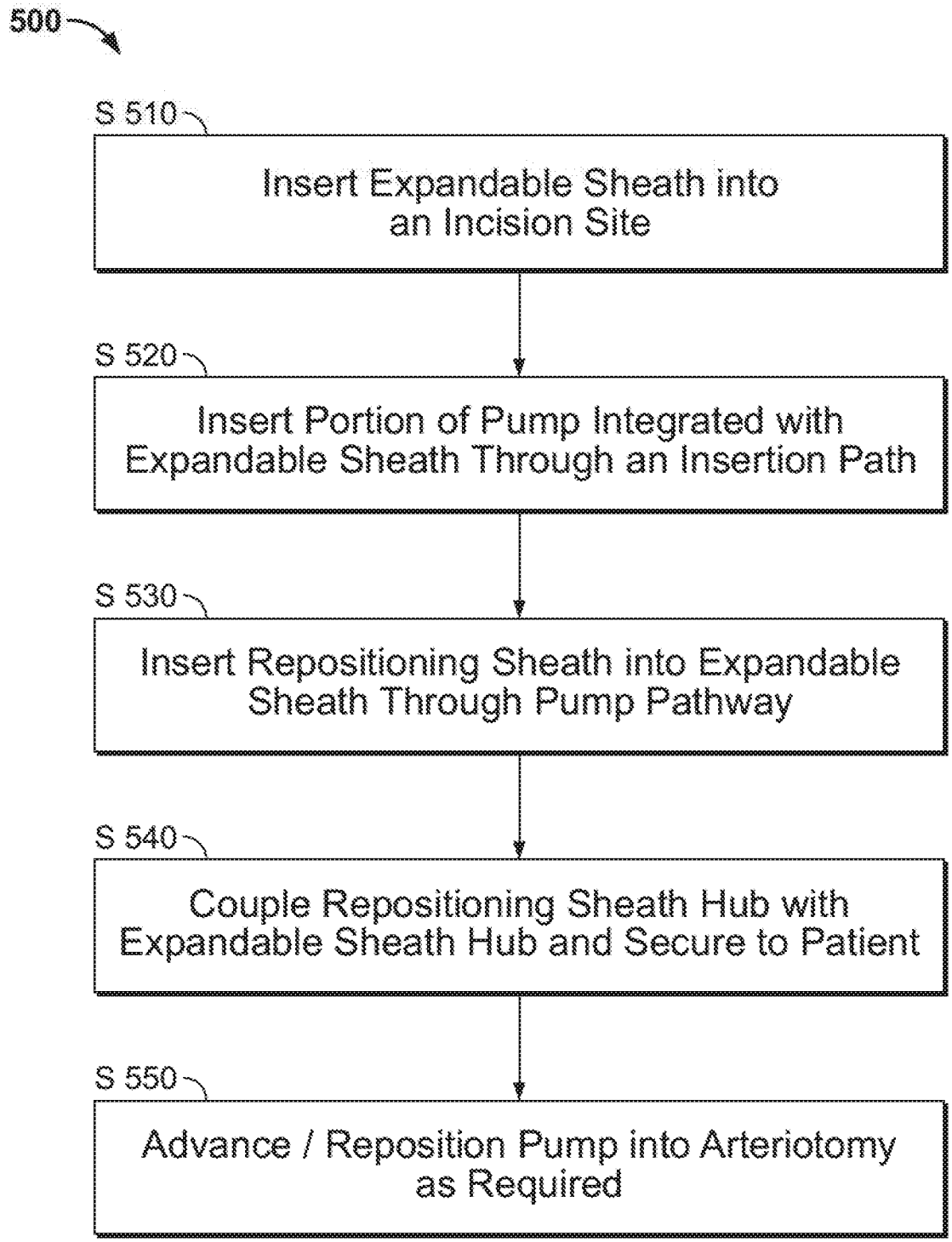
FIG. 5 shows an illustrative method for inserting a pump into an arteriotomy using the expandable sheath of FIG. 4.

FIG. 5 shows a method 500 of using an expandable access assembly. At step S510, an expandable sheath (e.g., the expandable sheath 400 of FIG. 4) is inserted into the patient through an insertion site (e.g., insertion site 650 of FIG. 6) with the aid of a vascular dilator (e.g., vascular dilator 600 of FIG. 600). Such insertion sites are made during surgery and may comprise a key-hole incision, for example.

Figure 8:
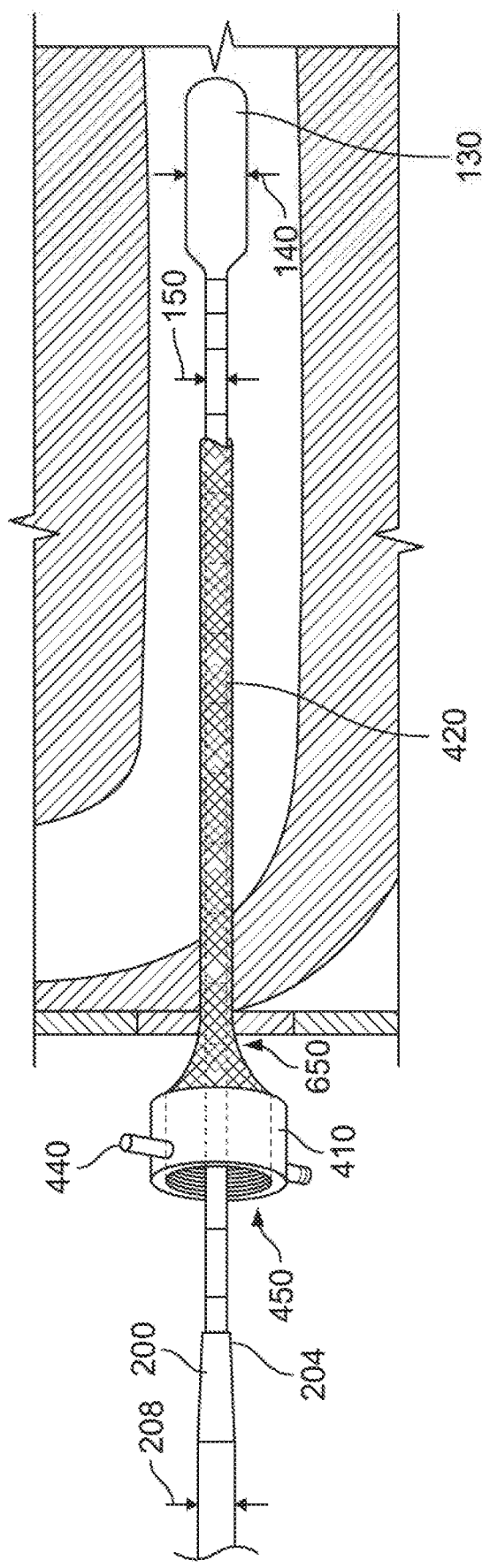
FIG. 8 shows a perspective view of the illustrative repositioning sheath of FIG. 3 being inserted into the expandable sheath of FIG. 4 after the medical device of FIG. 1 has completely passed through the expandable sheath.

In step S520, a pump head (e.g., pump head 130) and a portion of a pump body (e.g., a portion of pump body 120) is threaded through an opening in the hub (e.g., opening 450 in hub 410) of the expandable sheath. As the pump head advances through the lumen of the expandable sheath (e.g., lumen 430 of expandable sheath 400), it causes the expandable body (e.g., expandable body 420) to increase in diameter. Due to its compliant nature, the expandable body conforms to the shape of the pump head as it is advanced through the lumen of the expandable sheath. Additionally, the pressure of the blood within the patient may exert a compressive force on the expandable body which can assist with the conformity of the expandable body to the shape of the pump head. The pump head is advanced until it exits the distal portion of the expandable body (e.g., distal portion 404 of expandable body 420 as shown in FIG. 8). When the pump head leaves the expandable body, the lumen of the expandable body substantially returns to its unexpanded diameter.

In step S530, after the percutaneous pump has been advanced past the distal portion of the expandable body, the repositioning sheath (e.g., repositioning sheath 200) is advanced into the vasculature of the patient. Here, the repositioning sheath is threaded along the body of the percutaneous pump where the distal portion is inserted into the opening of the hub (e.g., opening 450) of the expandable sheath. A medical professional may use the hub 210 of the repositioning sheath 200 to advance the repositioning sheath into the expandable sheath 400.

In step S540, the repositioning sheath hub (e.g., hub 210) is coupled with the hub of the expandable sheath (e.g., hub 410). Such coupling may be achieved using any kind of engaging mechanism such as a threaded connection, a press fit connection or a clip-lock connection, for example. As exemplified in FIG. 9, the hub 410 of the expandable sheath has an internal fit with the repositioning sheath hub 210, i.e. hub 410 of the expandable sheath fits within the repositioning sheath hub 210 when the hubs are coupled. In other implementations (not shown), the repositioning sheath hub 210 has an internal fit with the hub 410 of the expandable sheath, i.e. the repositioning sheath hub 210 fits within the hub 410 of the expandable sheath when the hubs are coupled. Once coupled, the first lumen 230 of the repositioning sheath 200 may be in fluid communication with the lumen 430 of the expandable sheath 400.

In step S550, the distal portion of the repositioning sheath (e.g., distal portion 204) is advanced into the arteriotomy from within the lumen of the expandable sheath (e.g., lumen 430). The graduation in the tapered surface (e.g., tapered surface 260) is inserted to the desired depth as necessary to plug the arteriotomy in a blood vessel (e.g., arteriotomy 1020 of FIG. 10). This seals the gap between the percutaneous pump and the arteriotomy and prevents any blood from pouring out of the arteriotomy.

The method 500 of FIG. 5 therefore ensures that when the repositioning sheath is inserted into the lumen of the expandable sheath, the repositioning sheath fills a space between the expandable sheath and the percutaneous pump. This prevents or reduces accumulation of blood between the second sheath and the percutaneous pump, thereby minimizing the risk of thrombus formation.

FIG. 6 shows a perspective view of the insertion of the illustrative expandable sheath 400 of FIG. 4 into an insertion site using a vascular dilator 600. The dilator 600 has a diameter that is smaller than the diameter 405 of the opening 450 at the proximal portion 402 of the expandable sheath 400. Prior to insertion into the insertion site 650, the dilator 600 is inserted into the expandable sheath through opening 450 and is advanced through the lumen 430 from the proximal portion 402 to the distal portion 404 of the expandable body 420. Inserting the dilator 600 into the lumen 430 of the expandable sheath 400 causes the diameter 425 of the expandable body 420 to increase so that the expandable sheath 400 conforms to the shape of the dilator 600. As depicted in FIG. 6, the dilator 600 is completely inserted into the expandable sheath 400.

Figure 7:
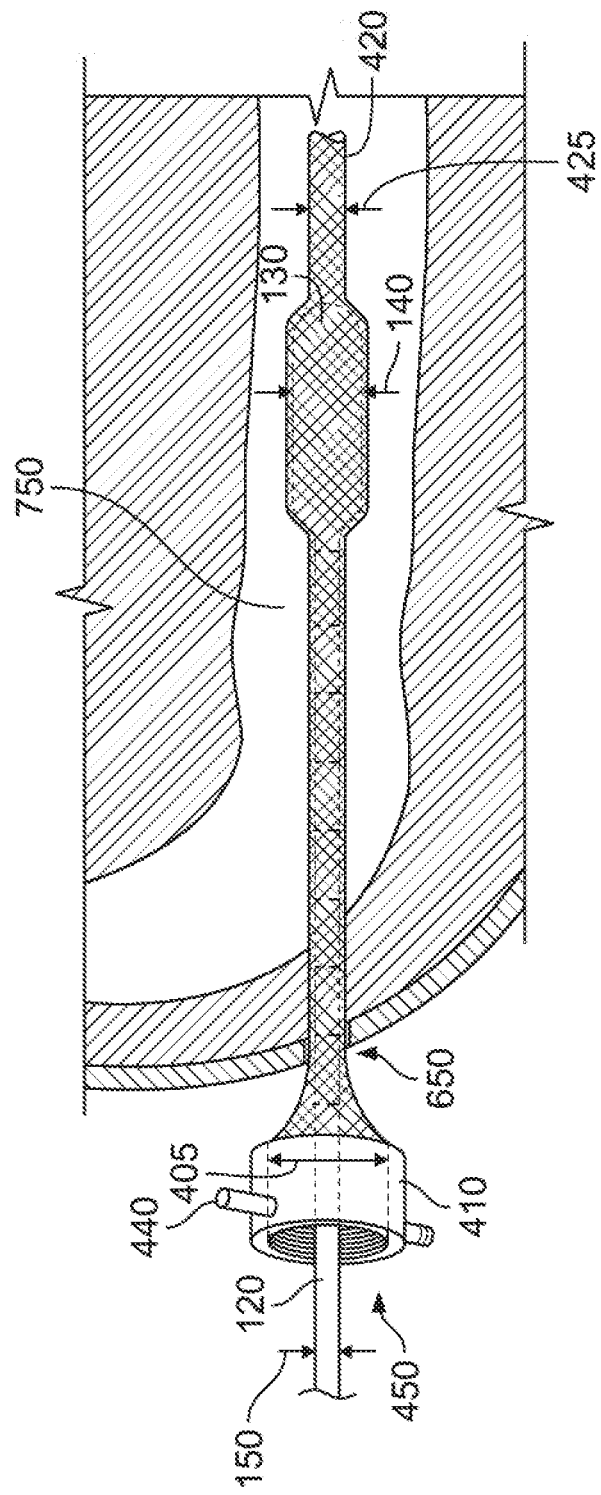
FIG. 7 shows a perspective view of the illustrative medical device of FIG. 1 being inserted into the expandable sheath of FIG. 4.

An outer surface of the dilator 600 may be coated with a hydrophilic coating or any other suitable coating to reduce frictional forces during insertion/removal of the dilator 600 from the expandable sheath 400. The outer surface of the dilator 600 may also be coated with a lubricating gel to ease insertion into the expandable sheath 400 and the insertion site 650. Once the dilator 600 is completely inserted into the expandable sheath 400, as depicted in FIG. 6, the arrangement is inserted into the insertion site 650, as shown in FIG. 7. Once the body 420 of the expandable sheath 400 is inserted in the insertion site 650, the dilator 600 is removed from the expandable sheath 400. When this happens, the expandable body 420 substantially returns to its unexpanded state within the vasculature of the patient.

FIG. 7 shows a perspective view of an illustrative expandable introducer inserted of the illustrative percutaneous medical device of FIG. 1 into the expandable sheath of FIG. 4. In the depicted position, the hub 410 of the expandable sheath 400 remains outside the patient while the expandable body 420 resides within the patient. FIG. 7 also shows that the integrated repositioning sheath 300 (not visible in this view) is advanced into the vasculature of the patient through the expandable sheath 400. As previously mentioned, the integrated repositioning sheath 300 comprises the repositioning sheath 200 fixed onto the pump body 120 of the percutaneous pump 100. As the pump head 130 advances through the lumen 430 of the expandable sheath 400, it causes the expandable body 420 to increase in diameter as shown in FIG. 7. Due to its compliant nature, the body 420 conforms to the shape of the pump head 130 as it is advanced through the lumen 430. Additionally, the pressure of the blood 750 within the patient may exert a compressive force on the expandable body 420 which would assist with the conformity of the expandable body 420 to the shape of the pump head 130. The pump head 130 is advanced until it exits the distal portion 404 of the expandable body 420 as shown in FIG. 8.

FIG. 8 shows a perspective view of the insertion of the illustrative repositioning sheath of FIG. 3 into the expandable sheath of FIG. 4 after the percutaneous medical device of FIG. 1 has completely passed through the expandable sheath. FIG. 8 shows that when the pump head 130 leaves the expandable body 420, the lumen 430 of the expandable body 420 substantially returns to its unexpanded diameter 425. After the percutaneous pump 100 has been advanced past the distal portion 404 of the expandable body 420, the repositioning sheath 200 is advanced into the vasculature of the patient. The repositioning sheath 200 is threaded along the body 120 of the percutaneous pump 100, with the distal portion 204 being inserted into the opening 540 of the hub 410 of the expandable sheath 400. The hub 210 of the repositioning sheath 200 may be used to advance the repositioning sheath into the expandable sheath 400.

Figure 9:
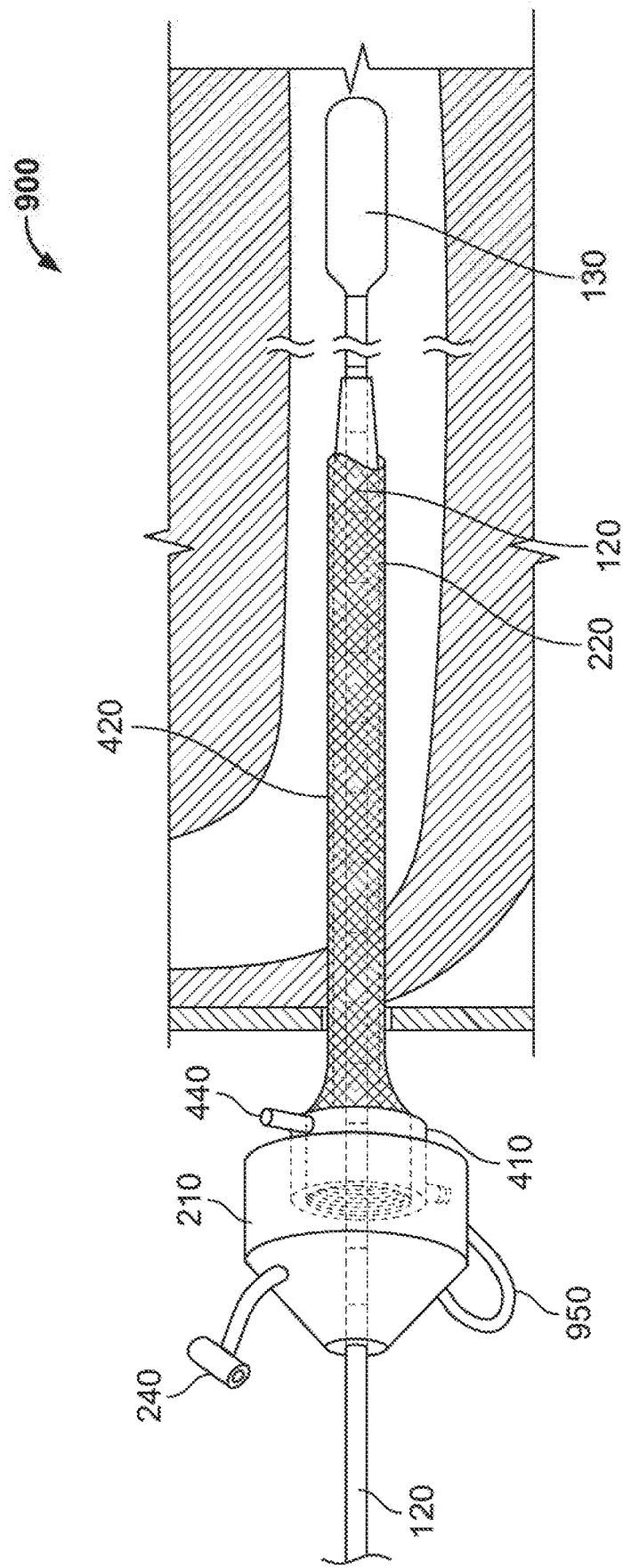
FIG. 9 shows the illustrative expandable sheath assembly when the repositioning sheath of FIG. 2 is advanced towards the medical device of FIG. 1 and a hub on the proximal end of the repositioning sheath is coupled with a hub on the proximal end of the expandable sheath.

FIG. 9 shows the illustrative expandable sheath assembly when the repositioning sheath of FIG. 2 is advanced towards the percutaneous medical device of FIG. 1 in which a hub on the proximal end of the repositioning sheath is coupled with a hub on the proximal end of the expandable sheath.

FIG. 9 depicts the expandable access assembly 900 after the repositioning sheath 200 is fully inserted into the expandable sheath 400. The hub 410 of the expandable sheath 400 and the hub 210 of the repositioning sheath 200 are coupled. Such coupling may be achieved using any kind of engaging mechanism such as a threaded connection, a press fit connection or a clip-lock connection, for example. In some implementations, the coupling between the expandable sheath and the repositioning sheath can be hemostatic and designed with a sealing feature such as an O-ring or interference fit to prevent blood leaking between the sheaths and the catheter. Once coupled, the first lumen 230 of the repositioning sheath 200 is in fluid communication with the lumen 430 of the expandable sheath 400.

The expandable access assembly 900 is advantageous over conventional peel-away introducer sheaths in that the expandable sheath 400 does not need to be separated or taken apart to make way for the repositioning sheath 200. Such separation requires force which may inadvertently dislodge the position of the percutaneous pump 100. Additionally, the integrated expandable sheath assembly of the present disclosure can be fixed in place on the skin of a patient and used repeatedly when the percutaneous pump needs to be repositioned.

Figure 10:
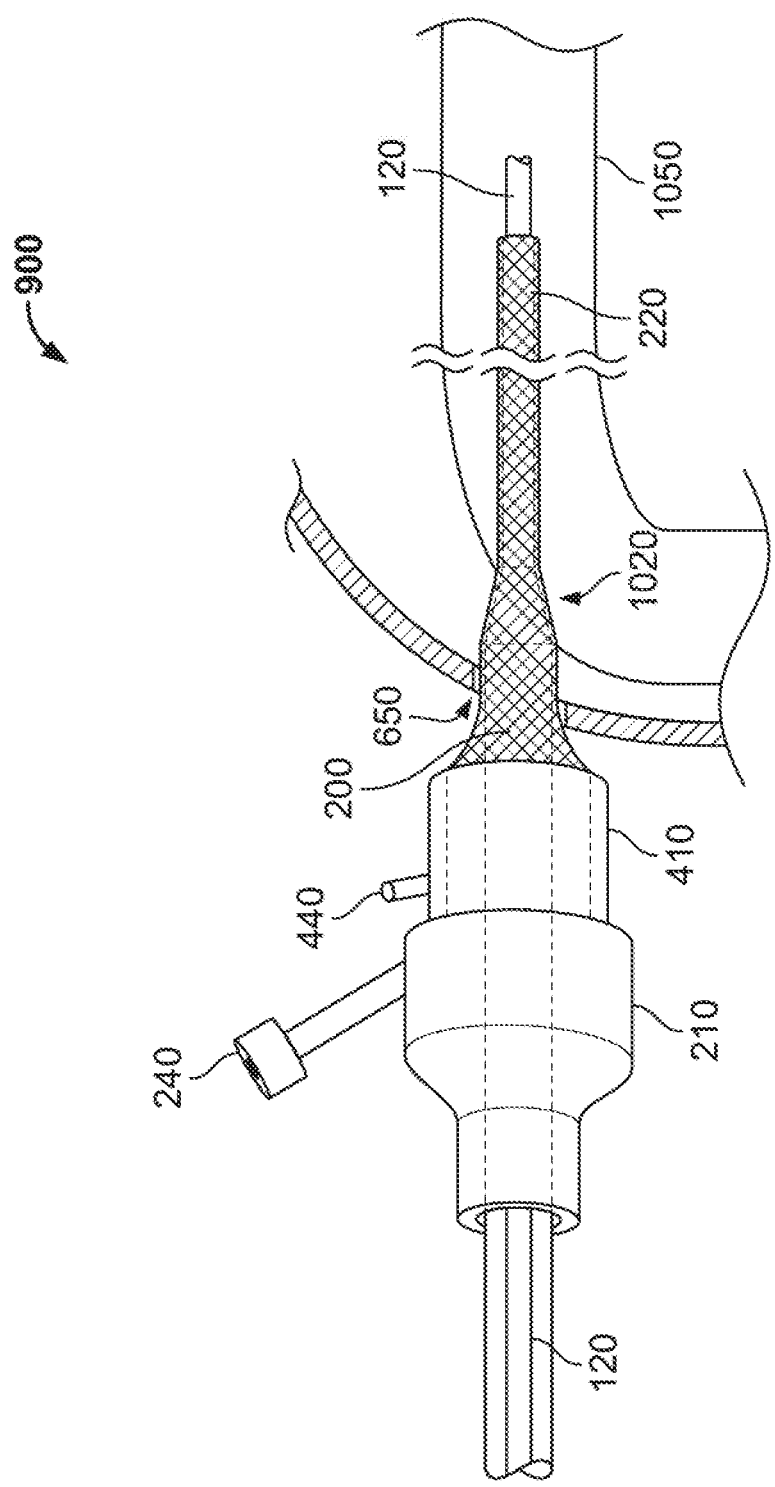
FIG. 10 shows a perspective view of the illustrative expandable sheath of FIG. 4 inserted into a blood vessel through an arteriotomy.

FIG. 10 shows a perspective view of the illustrative expandable sheath 400 of FIG. 4 inserted into a blood vessel through an arteriotomy. Once the hub 210 of the repositioning sheath 200 and the hub 410 of the expandable sheath 400 are coupled, the distal portion 204 of the repositioning sheath 200 is advanced into the arteriotomy from within the lumen 430 of the expandable sheath 400. The graduation in the tapered surface 260 can be inserted to the desired depth as necessary to plug the arteriotomy 1020 in a blood vessel 1050. This seals the gap between the percutaneous pump 100 and the arteriotomy 1020 and prevents blood from pouring out of the arteriotomy. Once the expandable access assembly 900 is in position, the percutaneous pump 100 (not shown) can be repositioned within a blood vessel as required without having to move the assembly 900. This can be done by simply sliding the pump body 120 proximally and/or distally along the first lumen 230 of the repositioning sheath 200 when the assembly 900 is fixed in position relative to the body of the patient.

Once the assembly 900 is in place, the hub 210 of the repositioning sheath 200 can be anchored to the patient. As previously mentioned, the hub 210 may include features for the attachment of sutures such as wings (e.g., feature 950 of FIG. 9) and suture holes (not shown). The suture holes allow the wings to be sutured to a patient to stabilize the assembly 900. Any suitable number of suture holes may be used. The hub 210 is also designed to be easily attached to a vascular graft with umbilical tape or sutures. This is beneficial during axillary insertions or any other insertions which require pump placement through a vascular graft. In certain implementations, other stabilizations devices, such as surgical tape, a STATLOCK® stabilization device (Bard Access Systems, Inc., Salt Lake City, Utah), or any other suitable adhesive stabilization device may be coupled to the hub 210.

It should be noted that the geometry of the arteriotomy 1020 may be such that a fluid-tight seal is not formed, thereby leading to seepage of blood from the blood vessel 1050 to the exterior of the arteriotomy 1020. Such geometries may be non-uniform, such as a non-circular opening in the blood vessel. This may lead to the formation of blood embolisms and blood clots which are undesirable. In accordance with the present disclosure, the expandable body 220 of the sheath 200 is able to expand as necessary with the internal blood pressure, enabling it to conform to a noncircular arteriotomy thereby preventing any seepage of blood. In certain implementations in which the repositioning sheath 200 has an inflatable balloon attached to the outer surface 206 of the sheath body 220 (as previously discussed), the balloon may be inflated to anchor the assembly 200. Additionally, the inflated balloon may further suppress any seepage of blood from an irregular arteriotomy by adjusting the diameter of the expandable sheath as required.

In order to further prevent thrombus formation within the expandable access assembly 900, port 440 on hub 410 allows for the connection of a pressure bag to flush the interior of the assembly 900 with a fluid to maintain the patency of the system. As previously mentioned, a pressure bag may be connected to these ports using any kind of engaging mechanism (e.g. threads, press-fit, clip lock, etc.). An infusion pump may be used in combination with the pressure bag to regulate the flow rate of liquid into the patient. For example, the flow rate may be limited to 1 mL/hr, 2 mL/hr, 5 mL/hr, 10 mL/hr, or any other suitable flow rate. In particular, the space between the expandable sheath 400 and the repositioning sheath 200 can be flushed with fluid introduced into the assembly via port 440. Such flushing may be instantaneous or continuous. By flushing these spaces with fluid, any thrombus formation in the insertion path of the percutaneous pump 100 will also be flushed away. The port can also be used to obtain measurement of blood pressure if necessary. Alternatively, the hub need not include this port.

Figure 11:
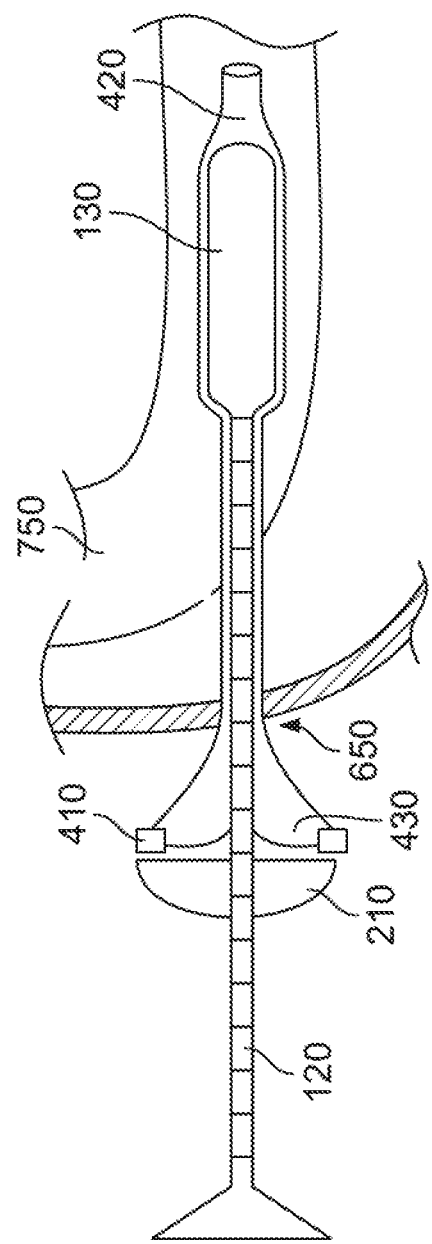
FIG. 11 shows an implementation of an illustrative alternative configuration of an expandable sheath assembly inserted into a blood vessel through an arteriotomy wherein the repositioning sheath of FIG. 3 comprises a hub.

In certain implementations, the repositioning sheath 200 may only comprise a second hub 210 which is fixedly attached to the pump body 120. In such a configuration, the expandable body 420 collapses completely onto the pump body 120 when the percutaneous pump 100 is inserted into the expandable sheath 400. The fixed second hub 210 allows the pump 100 to be maneuvered within the vasculature of a patient so as to be positioned in a blood vessel. The second hub 210 is then coupled to hub 410 of the expandable sheath 400 such that the hubs are in fluid communication with each other, and, more specifically, such that the second hub 210 is in fluid communication with lumen 430 of the expandable sheath 400, as shown in FIG. 11. In some implementations, the second hub 210 comprises a port or sidearm that is in fluid communication with a space between the expandable body 420 and the portion of the percutaneous pump 100 when the hub 410 is coupled to the second hub 210. Such a port may be used for flushing the space between the expandable body 420 and the portion of the percutaneous pump 100 with a fluid. Alternatively, the port could be used for the measurement of blood pressure.

In other implementations, no expandable sheath 400 is required. Instead the body 220 of the repositioning sheath 200 may be expandable. This allows the user to dial in the diameter of the sheath body 220 to fill any void between an arteriotomy and the percutaneous pump 100.

In some implementations, the expandable access assembly 1200 additionally includes a removable component such as a peel-away sheath 1210, as shown in FIG. 12. In such a configuration, the peel-away sheath 1210 is a rigid sheath that can be split or peeled away. Here the rigid sheath 1210 acts as a stiffening structure for delivery into the vessel while positioned inside the expandable sheath 400. The rigid sheath 1210 is then peeled away without disturbing the position of the medical device 100 relative to the patient. Once the rigid sheath 1210 is peeled away, a repositioning sheath 200 can then be advanced down the body 120 of the medical device 100 to fill the opening in the vessel.

Additionally, guidewire access through the second lumen 250 of the repositioning sheath 200 is also possible when the assembly 900 is in position in the vasculature of the patient.

In view of the foregoing, it will become abundantly clear that the present disclosure provides a means to fixate mechanical assist devices in place within an integrated expandable sheath anchored to the patient, thereby preventing the migration of the device once inserted into the heart.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system percutaneous heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

We claim:

1. A sheath assembly comprising:
   a medical device configured to be inserted into a blood vessel, a first portion of the medical device having a first width, and a second portion of the medical device having a second width that is smaller than the first width;
   a first sheath having a first lumen extending between proximal and distal ends of the first sheath configured to allow for passage of the second portion of the medical device;
   a first hub coupled to the proximal end of the first sheath;
   a second sheath having a second lumen extending between proximal and distal ends of the second sheath, the second lumen being expandable; and
   a second hub coupled to the proximal end of the second sheath,
   wherein the second lumen is configured to have a first inner diameter at rest, and to elastically expand from the first inner diameter to a second inner diameter during passage of the first portion of the medical device,
   wherein the second lumen is configured to contract from the second inner diameter to the first inner diameter during the passage of the second portion of the medical device, leaving a gap between an inner surface of the second sheath and an outer surface of the second portion of the medical device, and
   wherein the first sheath is configured to fill the gap and form a seal between the inner surface of the second sheath and the second portion of the medical device when the second sheath is inserted in the blood vessel and the first sheath is inserted into the second lumen over the second portion of the medical device, such that blood from the blood vessel is substantially prevented from migrating past the seal.

2. The sheath assembly of claim 1, further comprising a port configured to enable delivery of a fluid between an inner surface of the first sheath and the outer surface of the second portion of the medical device when the second portion of the medical device is contained within the first lumen.

3. The sheath assembly of claim 2, wherein the port is located on the first hub.

4. The sheath assembly of claim 1, further comprising a port configured to enable delivery of a fluid between the inner surface of the second sheath and an outer surface of the first sheath when the first sheath is inserted into the second lumen.

5. The sheath assembly of claim 4, wherein the port is located on the second hub.

6. The sheath assembly of claim 1, wherein the first hub further comprises a port configured to enable delivery of a fluid into the second lumen of the second sheath when the first sheath is inserted into the second lumen.

7. The sheath assembly of claim 1, wherein the first sheath further comprises an auxiliary lumen substantially parallel to the first lumen and extending from the proximal end to the distal end of the first sheath, the auxiliary lumen configured to allow for passage of a guidewire.

8. The sheath assembly of claim 7, wherein the first hub further comprises a port in communication with the auxiliary lumen, the port configured to allow for the passage of the guidewire.

9. The sheath assembly of claim 1, wherein an outer surface of the first sheath is tapered from the proximal end to the distal end of the first sheath, an outer diameter of the first sheath at the proximal end of the first sheath being larger than an outer diameter of the first sheath at the distal end of the first sheath.

10. The sheath assembly of claim 1, wherein the first sheath further comprises an expandable balloon configured to enable varying of a diameter of the second lumen when the first sheath is inserted into the second lumen.

11. The sheath assembly of claim 10, wherein the first hub comprises a balloon port in communication with the expandable balloon.

12. The sheath assembly of claim 1, wherein the first hub and the second hub are configured to couple to each other via at least one of: a threaded connection, a press fit connection or a cliplock connection.

13. The sheath assembly of claim 1, wherein the first hub includes a feature configured for suturing to a patient.

14. The sheath assembly of claim 13, wherein the feature configured for suturing to the patient includes a pair of suture wings.

15. The sheath assembly of claim 1, wherein an outer diameter of the second sheath is dimensioned to be introduced through a percutaneous access site of about 20 Fr (6.67 mm) or less.

16. The sheath assembly of claim 1, wherein the second sheath comprises either a porous material or a mesh material.

17. The sheath assembly of claim 1, wherein an outer surface of the first sheath comprises one of: radiopaque markers, visible markers, or markers for determining a depth of insertion.

18. The sheath assembly of claim 1, wherein an outer surface of the first sheath is coated with one of: an anti-thrombogenic coating, or a coating configured to reduce a likelihood of blood clot formation between the first sheath and the second sheath when inserted into the blood vessel.

19. The sheath assembly of claim 1, wherein an outer surface of the second sheath is coated with one of: a hydrophilic coating, a hydrophobic coating, or a coating to reduce friction.

20. The sheath assembly of claim 1, wherein an outer surface of the second sheath is coated with one of: an antimicrobial coating, or a coating configured to reduce a likelihood of infection occurring in the blood vessel when the second sheath is inserted into the blood vessel.

21. The sheath assembly of claim 1, wherein the first sheath is configured to be inserted into the second sheath by moving the first sheath and the second sheath axially relative to one another along a longitudinal axis of the first sheath and the second sheath.

22. The sheath assembly of claim 21, wherein both of the first sheath and the second sheath are configured to be slidably coupled to the second portion of the medical device.

23. The sheath assembly of claim 22, wherein the medical device is a percutaneous heart pump.

24. The sheath assembly of claim 1, wherein the second sheath is configured to be expandable by blood pressure within the blood vessel so as to seal a space between an outer surface of the second sheath and an arteriotomy in the blood vessel.

25. The sheath assembly of claim 1, further comprising:
a rigid third sheath having a third lumen extending between proximal and distal ends of the third sheath configured to allow for the passage of the first portion and the passage of the second portion of the medical device,
wherein the third sheath is configured to be inserted into the second sheath and to allow insertion of the first portion of the medical device into the blood vessel, and
wherein the third sheath is a peel-away sheath configured to be removable from the medical device while the first portion of the medical device remains positioned in the blood vessel.

* * * * *

UNITED STATES PATENT AND TRADEMARK OFFICE
CERTIFICATE OF CORRECTION

PATENT NO. : 11,197,690 B2
APPLICATION NO. : 16/130475
DATED : December 14, 2021
INVENTOR(S) : Glen R. Fantuzzi et al.

It is certified that error appears in the above-identified patent and that said Letters Patent is hereby corrected as shown below:

In the Drawings

Sheet 4 of 11, Fig. 5:
Now reads: "S 510"; should read -- S510 --

Sheet 4 of 11, Fig. 5:
Now reads: "S 520"; should read -- S520 --

Sheet 4 of 11, Fig. 5:
Now reads: "S 530"; should read -- S530 --

Sheet 4 of 11, Fig. 5:
Now reads: "S 540"; should read -- S540 --

Sheet 4 of 11, Fig. 5:
Now reads: "S 550"; should read -- S550 --

In the Specification

Column 8, Line 1:
Now reads: "270"; should read -- 230 --

Column 8, Line 2:
Now reads: "280"; should read -- 250 --

Column 9, Line 34:
Now reads: "420."; should read -- 220. --

Column 10, Line 1:
Now reads: "FIG. 600)."; should read -- FIG. 6). --

Signed and Sealed this
Second Day of August, 2022

Katherine Kelly Vidal
*Director of the United States Patent and Trademark Office*

CERTIFICATE OF CORRECTION (continued)
U.S. Pat. No. 11,197,690 B2

Column 13, Line 1:
Now reads: "220"; should read -- 420 --

Column 13, Line 9:
Now reads: "200."; should read -- 900. --